(12) United States Patent
Kaack et al.

(10) Patent No.: US 9,535,040 B2
(45) Date of Patent: Jan. 3, 2017

(54) METHOD FOR TESTING CONNECTIONS OF METAL WORKPIECES TO PLASTIC COMPOUNDS FOR CAVITIES BY MEANS OF ULTRASOUND

(75) Inventors: Michael Kaack, Bochum (DE); Christian Kremer, Braunschweig (DE); Jörn Winkels, Werl (DE); Holger Brauer, Gelsenkirchen (DE)

(73) Assignee: SALZGITTER MANNESMANN LINE PIPE GMBH, Siegen (DE)

(*) Notice: Subject to any disclaimer, the term of this patent is extended or adjusted under 35 U.S.C. 154(b) by 530 days.

(21) Appl. No.: 13/516,462

(22) PCT Filed: Nov. 29, 2010

(86) PCT No.: PCT/DE2010/001406
§ 371 (c)(1),
(2), (4) Date: Aug. 2, 2012

(87) PCT Pub. No.: WO2011/072638
PCT Pub. Date: Jun. 23, 2011

(65) Prior Publication Data
US 2012/0318064 A1 Dec. 20, 2012

(30) Foreign Application Priority Data
Dec. 17, 2009 (DE) .................. 10 2009 060 106

(51) Int. Cl.
*G01N 29/04* (2006.01)
*G01N 29/34* (2006.01)

(52) U.S. Cl.
CPC .......... *G01N 29/043* (2013.01); *G01N 29/343* (2013.01); *G01N 29/348* (2013.01); *G01N 2291/0231* (2013.01); *G01N 2291/044* (2013.01)

(58) Field of Classification Search
USPC .................. 73/588, 615, 587, 584
See application file for complete search history.

(56) References Cited

U.S. PATENT DOCUMENTS 3,640,122 A * 2/1972 Nusbickel, Jr. ................ 73/609
3,813,926 A * 6/1974 Stubbeman .................... 73/609
(Continued)

FOREIGN PATENT DOCUMENTS

DE    40 15 847 A1    11/1991
FR    2 756 632 A1    6/1998
(Continued)

OTHER PUBLICATIONS

FR2756632_English Translation.*
(Continued)

*Primary Examiner* — Paul West
*Assistant Examiner* — Xin Zhong
(74) *Attorney, Agent, or Firm* — Henry M. Feiereisen LLC

(57) ABSTRACT

The invention relates to a method for testing connections of metal workpieces to plastic compounds for cavities by means of ultrasound, wherein the plastic compound is arranged between the workpiece as an intermediate layer or is connected to the workpiece on one side and the cavity is located within the plastic compound, wherein the cavity is connected to the workpiece by means of a remaining plastic layer or plastic skin and wherein the plastic compound is exposed to ultrasonic signals of a certain test frequency and pulse length from the metal side of the workpiece by means of at least one ultrasonic probe, and in particular the ultrasonic signals reflected by flaws in the plastic compound are detected by the same or another ultrasonic probe and converted into electrical signals that can be evaluated and subjected to a threshold observation. The test frequency of (Continued)

the ultrasonic signals is set in a range of 1 to 10 MHz so that the attenuation of the sound is minimal after passing through the plastic skin.

5 Claims, 2 Drawing Sheets

(56) References Cited

U.S. PATENT DOCUMENTS

| | | | |
|---|---|---|---|
| 4,184,373 A * | 1/1980 | Evans et al. | 73/588 |
| 5,280,724 A * | 1/1994 | Higo et al. | 73/624 |
| 6,887,020 B2 | 5/2005 | Winkels et al. | |
| 2010/0219818 A1 | 9/2010 | Fischer et al. | |

FOREIGN PATENT DOCUMENTS

| | | |
|---|---|---|
| FR | 2756632 A1 * | 6/1998 |
| JP | 57-37257 A | 3/1982 |
| JP | 2000-221173 A | 8/2000 |

OTHER PUBLICATIONS

D. Yan et al.: Measurement of the ultrasonic nonlinearity of kissing bonds in adhesive joints, NDT&E International, Butterworth-Heinemann, vol. 42, No. 5, Jul. 1, 2009, pp. 459-466.

* cited by examiner

METHOD FOR TESTING CONNECTIONS OF METAL WORKPIECES TO PLASTIC COMPOUNDS FOR CAVITIES BY MEANS OF ULTRASOUND

CROSS-REFERENCES TO RELATED APPLICATIONS

This application is the U.S. National Stage of International Application No. PCT/DE2010/001406, filed Nov. 29, 2010, which designated the United States and has been published as International Publication No. WO 2010/072638 and which claims the priority of German Patent Application, Serial No. 10 2009 060 106.6, filed Dec. 17, 2009, pursuant to 35 U.S.C. 119(a)-(d).

BACKGROUND OF THE INVENTION

The invention relates to a method for testing connections of metallic workpieces with plastic compounds for cavities using ultrasound.

Plastic compounds are to be understood in the following as relating to any type of plastics which may find application e.g. as adhesive for bonding metallic workpieces, as seal, or as coating materials for metallic workpieces. For example, these materials are used for realizing adhesive bonds when metal sheets or tubes are involved or coating thereof.

When workpieces, such as for example metal sheets or tubes, are coated with a plastic, the application may cause defects in the form of e.g. cavities (air bubbles) in the coating or as a non-adherent connection at the contact point between coating and workpiece. Such defects can cause filiform corrosion of the workpiece and thus lead to a premature breakdown as a result of pitting corrosion.

When producing adhesive bonds, e.g. when tubes are involved, it is known to connect the tube ends with one another by means of a sleeve through introduction of adhesive into a joint gap between sleeve and tube.

Typical flaws of such bonds are for example air bubbles and non-adherent connection zones (so-called kissing bonds).

Strength tests of bonded tube connections have shown that these flaws for this application become critical only when exceeding a size of about 20 mm. It has been further shown that even though air bubbles in particular of this size normally fill the entire height of the joint gap, they are enveloped by a thin adhesive skin (100 μm-200 μm thickness) which adheres to the tube wall.

In order to ensure a sufficiently firm and flawless connection of the tubes, adhesive bonds are typically inspected by means of ultrasound using normal sound incidence. The sound is coupled into the first joint partner (sleeve) and travels there through. At the interface to the adhesive layer, part of the sound is reflected whereas another part penetrates the adhesive. The part that penetrates causes a further echo when reflected at the backside of the adhesive layer. In contrast thereto, the part that is reflected at the top surface of the adhesive layer causes in contrast thereto a long echo train through repeated reflections in the sleeve wall.

In the simplest solution of ultrasonic inspection of adhesive bonds of tubes, as known from JP 57037257 A, amplitudes of the echo from the backside of the adhesive layer are used for analysis. Sound is hereby sent through the adhesive and the absence of the echo indicates a flaw.

In the evaluation of the reflected ultrasonic signals, the latter are converted into electric signals and selected, amplified, and evaluated via time windows and orifices. The evaluations relate to amplitudes of the signals and the running times between the signals.

The examined information, i.e. the amplitudes, limit value exceedance, running time, etc., is detected, analyzed, logged by an electronic data processor and displayed on a monitor.

Other solutions, known e.g. from JP 2000221173 A analyze echoes from the top surface of the adhesive layer. Evaluated are hereby in particular the shape of the echo signals to draw conclusions about the quality of the adhesive bond.

As the ultrasonic signals get substantially weaker also after the adhesive layer or the coating material has cured, all solutions based on through transmission have the drawback that the echoes from the bottom side of the adhesive layer or the coating material can become very small especially when greater layer thicknesses are involved.

Experiences have shown that echoes from the bottom side of the layer can no longer be detected when layer thicknesses of above few millimeters are involved. In addition, in the case of adhesive sleeve bonds, the small back side echo superimposes the echo train from the sleeve which echo train produces in turn great amplitudes.

The methods based on the detection of the phase of the echo from the top surface of the adhesive layer suffer several shortcomings. On one hand, the reliable automated detection of the phase position is very difficult. On the other hand, there is no change in the phase position at the transition steel/plastic to steel/cavity especially for metallic workpieces as a result of the great acoustic density.

Further complicating the situation is the fact that formed cavities are always located inside the plastic compound and a thin layer of the plastic compound also always exists at the interface to the metallic workpiece in the form of a skin in surrounding relationship to the cavity so that the transition steel/cavity does not occur. The ultrasonic signals thus always impact the material combination steel/plastic/cavity in the presence of such flaws so that a meaningful ultrasonic inspection is complicated.

This is also a problem in the presence of air pockets in plastic coatings which may also be enveloped by a thin skin of plastic.

A change in the bonding or coating parameters (thickness of the adhesive layer or coating, condition of the workpiece surface, etc.) causes fluctuations of the ultrasonic signals which can easily lead to misinterpretations when undertaking only localized analysis.

In summary, ultrasonic inspection faces the following problem when detecting flaws in connections of plastics with metallic workpieces:

1. Air bubbles developing during coating of a workpiece or during filling of a joint gap with adhesive are encountered within the plastic compound and have therefore at the interface to the workpiece always a plastic skin which seals off the cavity.
2. Even in the presence of such a cavity, there exists therefore always the transition steel/plastic but not the transition steel/air (cavity). The detection of air bubbles beneath the plastic compound is therefore complicated especially for methods which use the reflection from the interface in the metallic workpiece.
3. Changes of the thickness and surface condition of the metallic workpiece as well as interference effects cause variations of the echo amplitudes. The localized analysis of these amplitudes and their relationships in the absence of accounting for proximal criteria becomes therefore unreliable.

It is therefore an object of the invention to provide a reliable and cost-efficient method for testing connections of metallic workpieces with plastic compounds by means of ultrasound to obviate the drawbacks of the known methods so that cavities in the plastic layer can be unambiguously detected and evaluated.

SUMMARY OF THE INVENTION

This object is solved in accordance with the invention by setting the test frequency of the ultrasonic signals in a range between 1 and 10 MHz in such a way that attenuation of the sound is minimal at the interface steel/cavity after passing through the plastic skin.

According to a further configuration of the invention, the test frequency and the pulse length are readjusted after setting for a minimum attenuation such that compared to a flawless plastic compound a signal amplification or signal weakening is established as a result of interference between the signals reflected from the top side of the plastic skin at the interface steel/plastic skin and from the bottom side of the plastic skin at the interface plastic skin/cavity.

The advantage of the described invention is the realization of a reliable detection of cavities in the adhesive layer or in the coating material when using particular test and evaluation methods so that reliable conclusions can be drawn about the quality of the coating or the adhesive bond.

Exhaustive tests involving inspection for air bubbles in adhesive bonds and coatings have shown that the selection of the "right test frequencies" is of utmost importance.

Although the sound penetrates the plastic, it is greatly attenuated, with the attenuation being frequency-dependent. The test frequency is therefore selected initially such that the weakening of the sound remains small after passing through the plastic skin. The echo from the interface of the skin bottom side/air then interferes with the echo of the interface steel/skin top side in a reinforcing or weakening manner so that these significant amplitude changes can be analyzed. Tests have shown that test frequencies between 1 and 10 or 3-7 MHz are beneficial. Moreover, the pulse length and the test frequency should be selected such that the interference causes a great contrast in the signal amplitudes so as to enhance the ability to evaluate the ultrasonic signals. The pulse length should hereby amount to at least twice the remaining residual layer between cavity and workpiece.

However, the pulse length should be selected only so long as to prevent a superimposition with the next following ultrasonic signal so that the evaluation of the signals is not complicated.

Tests have also shown that the selection of the "right echo" for the evaluation of the signals is of great importance. Advantageously, the evaluation should therefore involve the signals whose amplitude levels have the greatest difference compared to flawless plastic compounds. Evaluations with the $6^{th}$ or a following echo show a greater contrast in the signal amplitudes than, for example, evaluations with the $2^{nd}$ echo and thus can be excellently analyzed Care should however always be taken that the signal-noise ratio decreases as the number of echoes rises. The selection of the echo being evaluated is therefore to be constantly adjusted to the respective test situation.

Variations of the bonding parameters, like thickness and surface conditions of the metallic workpiece, width of the joint gap, etc, or altered coating thickness may lead locally to test signals that resemble those of flaws, like e.g. air bubbles. As the changed parameters normally extend across a greater region of the workpiece, this method also advantageously enables a reliable separation between the two signals as a result of a two-dimensional representation and evaluation including consideration of proximal criteria.

As the method according to the invention analyzes echo amplitudes, care should also be taken to realize a good and uniform coupling. A precise mechanical guidance of the probe during scanning may assist in the detection of flaws.

Advantageously, this method also enables the application of so-called EMUS probes (electromagnetically excited ultrasound) which as opposed to the conventional piezo technique render a coupling possible in the absence of coupling means, like e.g. water.

BRIEF DESCRIPTION OF THE DRAWING

The invention will now be described in greater detail with reference to the figures. Same reference signs in different figures designate same components. It is shown in:

FIG. 1 shows schematically a typical adhesive bond of tubes, using a sleeve. The metallic tubes 1, 1' to be connected with one another through bonding are placed end-to end with their end faces in axial alignment, with interposition of a sealing ring 3. The sealing ring 3 is provided to prevent migration of adhesive 6 being introduced through the contact area into the tube 1, 1'.

DETAILED DESCRIPTION OF PREFERRED EMBODIMENTS

Figure 1:
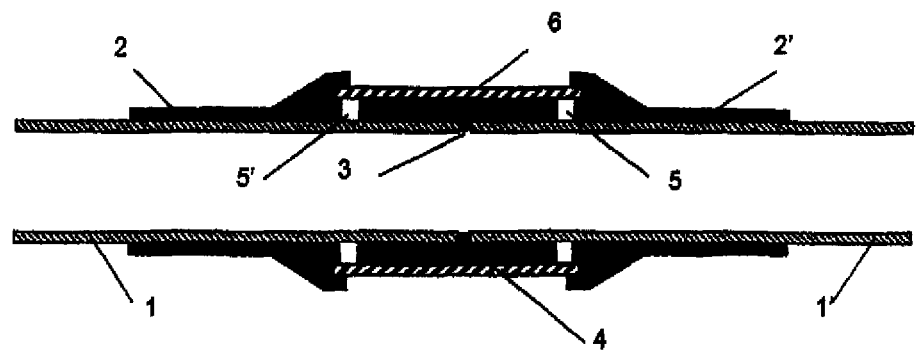
FIG. 1 a schematic illustration of a typical adhesive bond of tubes, using a sleeve, FIG. 2 an ultrasonic inspection of an adhesive bond according to FIG. 1, FIG. 3 an illustration of the amplitude relationships during an ultrasonic inspection according to FIG. 2.

A potting aid 2, 2' is arranged about the circumference on both sides of the tubes 1, 1' to hold a metallic sleeve 4 at a radial distance to the tube 1, 1' so as to form a cavity for introduction of the adhesive 6. The sleeve 4 covers the contact area of both tubes 1, 1', with the width of coverage being suited to the requirements at hand. The sleeve should be made of metal because the ultrasonic inspection of the adhesive bond can only be executed from the metallic side of the workpiece and is advantageously carried out from the outer side, when tube connections are involved. As an alternative, the adhesive bond could conceivably be tested also from the tube inner side, if this were to become necessary.

The potting aid 2, 2' is configured so as to radially surround the tube 1, 1' on one hand, and to be able to slide axially thereon—corresponding to the width of the sleeve 4, on the other hand. Spacers 5, 5' are respectively arranged in the region of the ends of the sleeve 4 on the circumference of the tubes 1, 1' to be able to adjust the radial distance of the sleeve 4 to the tube 1, 1', i.e. the radial width of the joint gap to be filled with adhesive 6.

Figure 2:
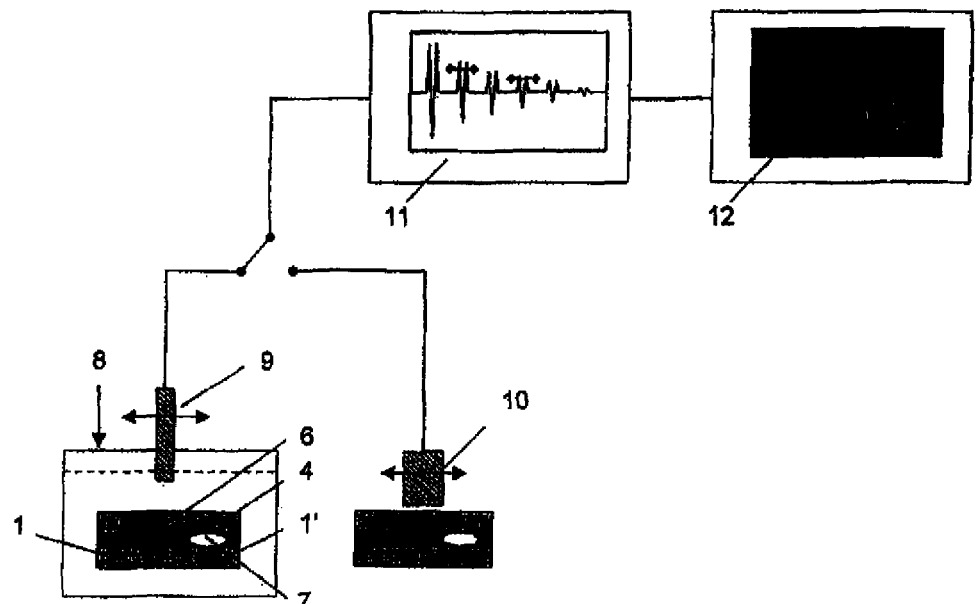

FIG. 2 shows schematically the ultrasonic inspection of an adhesive bond according to FIG. 1. The tube connection being tested is comprised of the two parts of the tubes 1, 1' which should be connected, the adhesive layer 6 (depicted with trapped air bubble 7), and the sleeve 4.

According to the left-hand bottom sub-image of FIG. 2, the tube connection is immersed during inspection with a piezo probe 9 in a test container 8, filled e.g. with water, or a sound coupling is realized in a suitable manner upon the test body using an immersion liquid. This is not necessary in the EMUS test technique illustrated in the right-hand bottom sub-image of FIG. 2; instead of a piezo probe 9 an EMUS probe 10 is used.

In both cases, the probe is guided for scanning across the sleeve 4. Pulses generated and received with the ultrasonic device 11 are recorded by a PC system 12. The amplitudes of selected echoes are evaluated, digitally filtered, and two-dimensionally illustrated.

In accordance with the invention, the test frequency of the ultrasonic signals is set to keep the attenuation of the sound as small as possible after passing through the plastic skin at the interface steel/cavity, and the test frequency and the pulse length are adjusted such that compared to a flawless plastic compound a signal amplification or signal weakening is established as a result of interference between the signals reflected from the top side of the plastic skin at the interface steel/plastic skin and from the bottom side of the plastic skin at the interface plastic skin/cavity.

Figure 3:
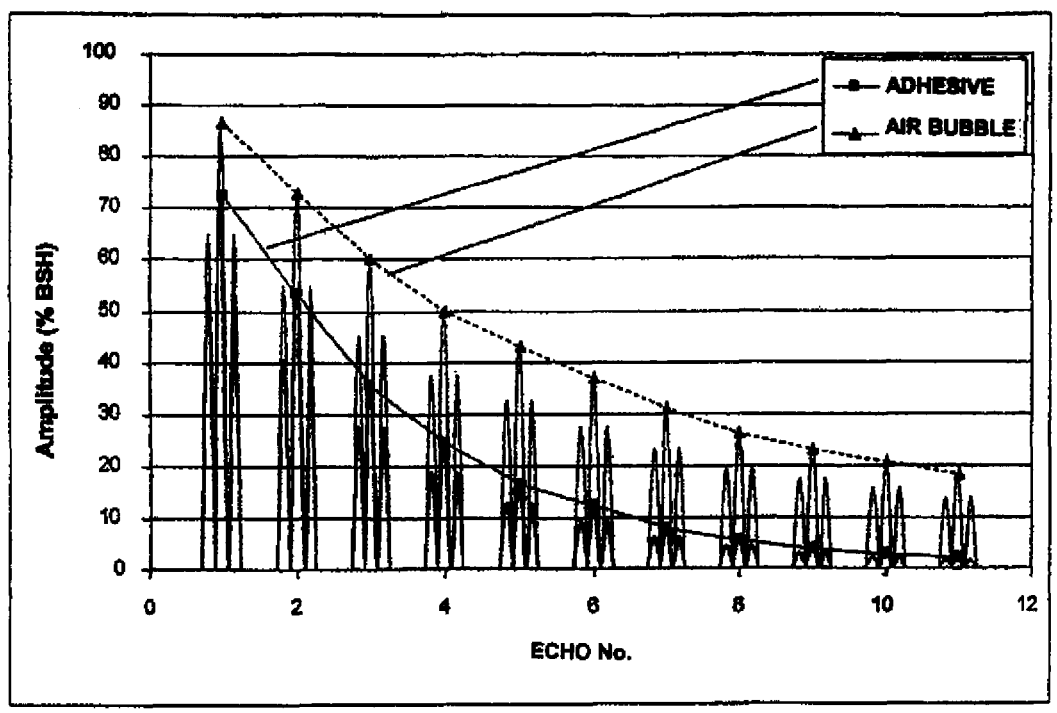

FIG. 3 shows the resultant illustration of the amplitude relationships as a function of the reflected echoes of the signal pulse. As can be seen, an increase in the echo number is accompanied by the significant increase of the contrast ratio of the amplitude signals from the adhesive and the air bubble so that the signal evaluation and therefore an unambiguous detection of trapped air bubbles in the plastic of the bond or the coating is made possible.

What is claimed is:

1. A method of testing a connection between a metallic workpiece and a plastic compound for the presence of a cavity in the connection, said method comprising:
    exposing the plastic compound to ultrasonic signals of a predefined test frequency and pulse length from a metal side of the workpiece, using at least one ultrasonic probe;
    detecting the ultrasonic signals reflected by a flaw in the plastic compound;
    converting the ultrasonic signals into electrical signals;
    subjecting the electrical signals to a threshold observation to determine whether the flaw indicates the presence of a cavity,
    wherein the test frequency of the ultrasonic signals is set in a range of 1 to 10 MHz such that attenuation of the ultrasonic signal is minimal after traveling through a plastic skin of the plastic compound; and
    exposing the plastic compound to ultrasonic signals from the metal side of the workpiece and using the at least one ultrasonic probe with test frequency and pulse length which are readjusted such that the presence of the cavity is determined by a signal amplification or signal weakening of electrical signals in comparison to the electrical signals generated by a flawless plastic compound as a result of interference between the readjusted ultrasonic signals reflected from a top side of the plastic skin at an interface between steel and plastic skin and from a bottom side of the plastic skin at an interface between plastic skin and cavity.

2. The method of claim 1, wherein the test frequency of the ultrasonic signals is set between 3 and 7 MHz.

3. The method of claim 1, wherein the predefined pulse length is set to a level which is at least twice a size of the remaining residual layer between the cavity and the workpiece.

4. The method of claim 1, wherein the predefined pulse length is sized long enough to prevent a superposition with a next following ultrasonic signal.

5. The method of claim 1, further comprising evaluating readjusted ultrasonic signals reflected from a top side of the cavity and from a bottom side of the cavity whose amplitude levels have a greatest difference compared to ultrasound signals reflected by a flawless region of the plastic compound while at the same time displaying a great signal/noise ratio.

* * * * *